United States Patent
Cherok et al.

(10) Patent No.: US 7,900,484 B2
(45) Date of Patent: Mar. 8, 2011

(54) PROSTHETIC REPAIR FABRIC

(75) Inventors: Dennis Cherok, Harrisville, RI (US); Rocco DiGregorio, Cliffwood, NJ (US); Alan Grumbling, Southampton, NJ (US); Michael Kirby, Edgewater Park, NJ (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 12/613,309

(22) Filed: Nov. 5, 2009

(65) Prior Publication Data
US 2010/0049222 A1    Feb. 25, 2010

Related U.S. Application Data

(63) Continuation of application No. 11/583,364, filed on Oct. 19, 2006, now Pat. No. 7,614,258.

(51) Int. Cl.
*D04B 21/00*    (2006.01)
(52) U.S. Cl. .......................................................... 66/192
(58) Field of Classification Search ................... 66/195, 66/192, 193, 202
See application file for complete search history.

(56) References Cited

U.S. PATENT DOCUMENTS

| | | |
|---|---|---|
| 2,671,444 A | 3/1954 | Pease, Jr. |
| 3,054,406 A | 9/1962 | Usher |
| 3,108,357 A | 10/1963 | Liebig |
| 3,124,136 A | 3/1964 | Usher |
| 3,272,204 A | 9/1966 | Artandi et al. |
| 3,276,448 A | 10/1966 | Kronenthat |
| 3,448,595 A | 6/1969 | Baltzer et al. |
| 3,463,158 A | 8/1969 | Schmitt et al. |
| 4,015,451 A | 4/1977 | Gajjar |
| 4,032,993 A | 7/1977 | Coquard et al. |
| 4,064,712 A | 12/1977 | Sayre et al. |
| 4,347,847 A | 9/1982 | Usher |
| 4,385,093 A | 5/1983 | Hubis |
| 4,452,245 A | 6/1984 | Usher |
| 4,478,665 A | 10/1984 | Hubis |
| 4,499,139 A | 2/1985 | Schortmann |
| 4,576,608 A | 3/1986 | Homsy |
| 4,596,728 A | 6/1986 | Yang et al. |
| 4,633,873 A | 1/1987 | Dumican et al. |
| 4,655,221 A | 4/1987 | Devereux |
| 4,695,500 A | 9/1987 | Dyer et al. |
| 4,769,038 A | 9/1988 | Bendavid et al. |
| 4,838,884 A | 6/1989 | Dumican et al. |
| 4,883,486 A | 11/1989 | Kapadia et al. |
| 4,955,907 A | 9/1990 | Ledergerber |
| 4,997,440 A | 3/1991 | Dumican |
| 5,002,551 A | 3/1991 | Linsky et al. |
| 5,007,916 A | 4/1991 | Linsky et al. |
| 5,092,884 A | 3/1992 | Devereux et al. |
| 5,116,360 A | 5/1992 | Pinchuk et al. |
| 5,222,987 A | 6/1993 | Jones |

(Continued)

FOREIGN PATENT DOCUMENTS

EP    0212604 A2    3/1987

(Continued)

*Primary Examiner* — Danny Worrell
(74) *Attorney, Agent, or Firm* — Wolf, Greenfield & Sacks, P.C.

(57) ABSTRACT

The repair fabric includes a dual bar warp knit mesh for use in repairing soft tissue and muscle wall defects, including hernia repair and chest wall reconstruction. The repair fabric may be produced according to a first bar pattern chain of 4/2 4/6 4/2 6/8 6/4 6/8 and a second bar pattern chain of 6/8 2/0 6/8 4/2 8/10 4/2.

11 Claims, 2 Drawing Sheets

U.S. PATENT DOCUMENTS

| | | | |
|---|---|---|---|
| 5,282,856 A | 2/1994 | Ledergerber |
| 5,292,328 A | 3/1994 | Hain et al. |
| 5,326,355 A | 7/1994 | Landi |
| 5,356,432 A | 10/1994 | Rutkow et al. |
| 5,366,504 A | 11/1994 | Andersen et al. |
| 5,368,602 A | 11/1994 | de la Torre |
| 5,424,117 A | 6/1995 | Heiman et al. |
| 5,456,711 A | 10/1995 | Hudson |
| 5,458,636 A | 10/1995 | Brancato |
| 5,461,885 A | 10/1995 | Yokoyama |
| 5,480,423 A | 1/1996 | Ravenscroft et al. |
| 5,554,437 A | 9/1996 | Gupta et al. |
| 5,569,273 A | 10/1996 | Titone et al. |
| 5,593,441 A | 1/1997 | Lichtenstein et al. |
| 5,611,127 A | 3/1997 | Ceriani et al. |
| 5,683,809 A | 11/1997 | Freeman et al. |
| 5,695,525 A | 12/1997 | Mulhauser et al. |
| 5,716,409 A | 2/1998 | Debbas |
| 5,725,577 A | 3/1998 | Saxon |
| 5,732,572 A | 3/1998 | Litton |
| 5,743,917 A | 4/1998 | Saxon |
| 5,769,864 A | 6/1998 | Kugel |
| 5,916,225 A | 6/1999 | Kugel |
| 5,948,020 A | 9/1999 | Yoon et al. |
| 5,972,007 A | 10/1999 | Sheffield et al. |
| 5,990,378 A | 11/1999 | Ellis |
| 6,004,333 A | 12/1999 | Sheffield et al. |
| 6,042,592 A | 3/2000 | Schmitt |
| 6,066,776 A | 5/2000 | Goodwin et al. |
| 6,090,116 A | 7/2000 | D'Aversa et al. |
| 6,113,623 A | 9/2000 | Sgro |
| 6,113,641 A | 9/2000 | Leroy et al. |
| 6,120,539 A | 9/2000 | Eldridge et al. |
| 6,136,024 A | 10/2000 | Shimizu |
| 6,143,025 A | 11/2000 | Stobie et al. |
| 6,162,537 A | 12/2000 | Martin et al. |
| 6,162,962 A | 12/2000 | Hinsch et al. |
| 6,171,318 B1 | 1/2001 | Kugel et al. |
| 6,176,863 B1 | 1/2001 | Kugel et al. |
| 6,176,875 B1 | 1/2001 | Lenker et al. |
| 6,179,872 B1 | 1/2001 | Bell et al. |
| 6,192,944 B1 | 2/2001 | Greenhalgh |
| 6,221,102 B1 | 4/2001 | Baker et al. |
| 6,251,132 B1 | 6/2001 | Ravenscroft et al. |
| 6,253,581 B1 | 7/2001 | Rhode et al. |
| 6,258,124 B1 | 7/2001 | Darois et al. |
| 6,264,702 B1 | 7/2001 | Ory et al. |
| 6,268,544 B1 | 7/2001 | Court et al. |
| 6,270,530 B1 | 8/2001 | Eldridge et al. |
| 6,280,453 B1 | 8/2001 | Kugel et al. |
| 6,287,316 B1 | 9/2001 | Agarwal et al. |
| 6,315,791 B1 | 11/2001 | Gingras et al. |
| 6,319,264 B1 | 11/2001 | Tormala et al. |
| 6,375,662 B1 | 4/2002 | Schmitt |
| 6,383,201 B1 | 5/2002 | Dong |
| 6,391,060 B1 | 5/2002 | Ory et al. |
| 6,408,656 B1 | 6/2002 | Ory et al. |
| 6,443,964 B1 | 9/2002 | Ory et al. |
| 6,447,551 B1 | 9/2002 | Goldmann |
| 6,488,801 B1 | 12/2002 | Bodaghi et al. |
| 6,521,555 B1 | 2/2003 | Bodaghi et al. |
| 6,537,313 B2 | 3/2003 | Ketharanathan |
| 6,540,773 B2 | 4/2003 | Dong |
| 6,547,820 B1 | 4/2003 | Staudenmeier |
| 6,554,855 B1 | 4/2003 | Dong |
| 6,596,002 B2 | 7/2003 | Therin et al. |
| 6,610,006 B1 | 8/2003 | Amid et al. |
| 6,630,414 B1 | 10/2003 | Matsumoto |
| 6,638,284 B1 | 10/2003 | Rousseau et al. |
| 6,652,574 B1 | 11/2003 | Jayaraman |
| 6,652,595 B1 | 11/2003 | Nicolo |
| 6,668,598 B2 | 12/2003 | Miyake et al. |
| 6,669,706 B2 | 12/2003 | Schmitt et al. |
| 6,673,102 B1 | 1/2004 | Vonesh et al. |
| 6,679,913 B2 | 1/2004 | Homsy |
| 6,706,376 B1 | 3/2004 | von Fransecky |
| 6,711,919 B1 | 3/2004 | Arnold et al. |
| 6,723,133 B1 | 4/2004 | Pajotin |
| 6,726,696 B1 | 4/2004 | Houser et al. |
| 6,736,823 B2 | 5/2004 | Darois et al. |
| 6,737,371 B1 | 5/2004 | Planck et al. |
| 6,755,867 B2 | 6/2004 | Rousseau |
| 6,755,868 B2 | 6/2004 | Rousseau |
| 6,783,554 B2 | 8/2004 | Amara et al. |
| 6,790,213 B2 | 9/2004 | Cherok et al. |
| 6,800,082 B2 | 10/2004 | Rousseau |
| 6,840,067 B2 | 1/2005 | Mass et al. |
| 6,841,492 B2 | 1/2005 | Bhatnagar et al. |
| 6,848,281 B2 | 2/2005 | Ishihara et al. |
| 6,946,003 B1 | 9/2005 | Wolowacz et al. |
| 6,971,252 B2 | 12/2005 | Therin et al. |
| 7,198,638 B2 | 4/2007 | Dong |
| 7,364,587 B2 | 4/2008 | Dong et al. |
| 7,402,174 B2 | 7/2008 | Dong |
| 2001/0049538 A1 | 12/2001 | Trabucco |
| 2001/0056303 A1 | 12/2001 | Caneiro et al. |
| 2002/0049503 A1 | 4/2002 | Milbocker |
| 2002/0049504 A1 | 4/2002 | Barault |
| 2002/0052612 A1 | 5/2002 | Schmitt et al. |
| 2002/0052654 A1 | 5/2002 | Darois et al. |
| 2002/0082707 A1 | 6/2002 | Homsy |
| 2002/0095218 A1 | 7/2002 | Carr, Jr. et al. |
| 2002/0103542 A1 | 8/2002 | Bilbo |
| 2002/0115369 A1 | 8/2002 | Yokoyama |
| 2002/0116070 A1 | 8/2002 | Amara et al. |
| 2002/0119177 A1 | 8/2002 | Bowman et al. |
| 2002/0120348 A1 | 8/2002 | Melican et al. |
| 2002/0147457 A1 | 10/2002 | Rousseau |
| 2002/0160679 A1 | 10/2002 | Yoon |
| 2002/0187694 A1 | 12/2002 | Brighton et al. |
| 2002/0193885 A1 | 12/2002 | Legeay et al. |
| 2002/0198588 A1 | 12/2002 | Armstrong et al. |
| 2003/0004581 A1 | 1/2003 | Rousseau |
| 2003/0028239 A1 | 2/2003 | Dong |
| 2003/0040809 A1 | 2/2003 | Goldmann et al. |
| 2003/0065248 A1 | 4/2003 | Lau et al. |
| 2003/0078602 A1 | 4/2003 | Rousseau |
| 2003/0100954 A1 | 5/2003 | Schuldt-Hempe et al. |
| 2003/0100955 A1 | 5/2003 | Greenawalt et al. |
| 2003/0114866 A1 | 6/2003 | Ulmsten et al. |
| 2003/0125796 A1 | 7/2003 | Dong |
| 2003/0130745 A1 | 7/2003 | Cherok et al. |
| 2003/0130747 A1 | 7/2003 | Abraham et al. |
| 2003/0134100 A1 | 7/2003 | Mao et al. |
| 2003/0149464 A1 | 8/2003 | Dong |
| 2003/0149490 A1 | 8/2003 | Ashman |
| 2003/0158607 A1 | 8/2003 | Carr et al. |
| 2003/0176912 A1 | 9/2003 | Chuter et al. |
| 2003/0181988 A1 | 9/2003 | Rousseau |
| 2003/0187516 A1 | 10/2003 | Amid et al. |
| 2003/0204235 A1 | 10/2003 | Edens et al. |
| 2003/0204241 A1 | 10/2003 | Dong |
| 2004/0029478 A1 | 2/2004 | Planck et al. |
| 2004/0034373 A1 | 2/2004 | Schuldt-Hempe et al. |
| 2004/0049260 A1 | 3/2004 | Dong |
| 2004/0054376 A1 | 3/2004 | Ory et al. |
| 2004/0059356 A1 | 3/2004 | Gingras |
| 2004/0138762 A1 | 7/2004 | Therin et al. |
| 2004/0172048 A1 | 9/2004 | Browning |
| 2004/0176658 A1 | 9/2004 | McMurray |
| 2004/0181288 A1 | 9/2004 | Darois et al. |
| 2004/0185734 A1 | 9/2004 | Gray et al. |
| 2004/0209538 A1 | 10/2004 | Klinge et al. |
| 2004/0211225 A1 | 10/2004 | Dickerson |
| 2004/0215219 A1 | 10/2004 | Eldridge et al. |
| 2004/0220610 A1 | 11/2004 | Kreidler et al. |
| 2004/0260315 A1 | 12/2004 | Dell et al. |
| 2005/0010239 A1 | 1/2005 | Chefitz |
| 2005/0021058 A1 | 1/2005 | Negro |
| 2005/0043818 A1 | 2/2005 | Bellon Caneiro et al. |
| 2005/0070829 A1 | 3/2005 | Therin et al. |
| 2005/0070930 A1 | 3/2005 | Kammerer |
| 2005/0222591 A1 | 10/2005 | Gingras et al. |
| 2005/0228408 A1 | 10/2005 | Fricke et al. |

FOREIGN PATENT DOCUMENTS

| | | |
|---|---|---|
| EP | 0303496 A1 | 2/1989 |
| EP | 0194192 A1 | 11/1989 |
| EP | 0537769 A1 | 4/1993 |
| EP | 0640329 | 3/1995 |
| EP | 0677297 A1 | 10/1995 |
| EP | 0692225 A2 | 1/1996 |
| EP | 0744162 A2 | 11/1996 |
| EP | 0797962 A2 | 10/1997 |
| EP | 0827724 A2 | 3/1998 |
| EP | 0927008 B1 | 7/1999 |
| EP | 0986993 A1 | 3/2000 |
| EP | 1022031 A1 | 7/2000 |
| EP | 1060714 A2 | 12/2000 |
| EP | 1140244 | 10/2001 |
| WO | WO 91/07145 | 5/1991 |
| WO | WO 94/01056 | 1/1994 |
| WO | WO 96/03091 A1 | 2/1996 |
| WO | WO 96/39999 | 12/1996 |
| WO | WO 98/37813 A1 | 9/1998 |
| WO | WO 01/15625 A1 | 3/2001 |
| WO | WO 01/80773 A1 | 11/2001 |
| WO | WO 02/30482 A1 | 4/2002 |
| WO | WO 02/091950 A1 | 12/2002 |
| WO | WO 03/003947 | 1/2003 |
| WO | WO 03/011183 | 2/2003 |
| WO | WO 03/075799 | 9/2003 |
| WO | WO 03/090643 | 11/2003 |
| WO | WO 2004/006808 | 1/2004 |
| WO | WO 2004/021933 | 3/2004 |
| WO | WO 2004/052421 | 6/2004 |
| WO | WO 2004/060211 | 7/2004 |
| WO | WO 2004/075936 | 9/2004 |

PROSTHETIC REPAIR FABRIC

RELATED APPLICATION(S)

This application is a continuation of U.S. application Ser. No. 11/583,364, filed Oct. 19, 2006.

FIELD OF INVENTION

The present invention relates to a prosthetic repair fabric, and more particularly to a prosthetic repair fabric for use in soft tissue and muscle wall repair.

BACKGROUND OF THE INVENTION

Implantable repair fabrics are employed by surgeons for soft tissue repair and reconstruction, including the repair of anatomical defects such as soft tissue and muscle wall defects. The fabric is typically sutured, stapled, tacked, or otherwise provisionally anchored in place over, under or within the defect. Tissue integration with the fabric, such as tissue ingrowth into and/or along the mesh fabric, eventually completes the repair.

Soft tissue and muscle wall defect repairs may be accomplished using various surgical techniques, including open, laparoscopic and hybrid (e.g., Kugel procedure) techniques. During open procedures, a repair fabric is placed through a relatively large incision made in the abdominal wall and layers of tissue and then the defect is filled or covered with the repair fabric. During laparoscopic and hybrid procedures, the fabric may be collapsed, such as by rolling or folding, into a reduced configuration for entry into a subject, either directly through a comparatively smaller incision or through a slender laparoscopic cannula that is placed through the incision.

Various repair fabrics are known and used for repairing soft tissue and muscle wall defects. BARD MESH and VISILEX, available from C.R Bard, are examples of implantable fabrics that have been successfully used in soft tissue and muscle wall repair. Such fabrics are fabricated from polypropylene monofilaments that are knitted into meshes having pores or interstices that promote tissue ingrowth and integration with the fabric.

Scar tissue may form about a repair fabric into a scar plate as tissue ingrowth occurs. The volume and rigidity of the scar plate that forms about the fabric may be affected by various factors, including the amount of foreign material introduced into a patient by the fabric.

It is an object of the invention to provide a prosthetic repair fabric for repair of soft tissue and muscle wall defects.

SUMMARY OF THE INVENTION

In one illustrative embodiment, an implantable prosthetic repair fabric comprises a biologically compatible, implantable dual bar warp knit mesh produced according to a first bar pattern chain of 4/2 4/6 4/2 6/8 6/4 6/8 and a second bar pattern chain of 6/8 2/0 6/8 4/2 8/10 4/2.

In one illustrative embodiment, an implantable prosthetic repair fabric comprises a knit mesh that includes a plurality of generally polygonal shaped primary pores defined by knitted strands of filaments. A pair of individual filaments extend across each primary pore to define a plurality of secondary pores within each primary pore. Each of the pair of individual filaments extend substantially parallel to one another.

DESCRIPTION OF THE DRAWINGS

Various embodiments of the invention will now be described, by way of example, with reference to the accompanying drawings, in which.

DETAILED DESCRIPTION

Embodiments of the present invention include a prosthetic fabric comprising a mesh fabric that is relatively flexible, thin and light weight and meets the performance and physical characteristics for soft tissue repair and reconstruction procedures. The surgical repair fabric may be used for reinforcing and closing soft tissue defects, and is particularly indicated for chest wall reconstruction and/or the repair of hernias, such as inguinal hernias. The mesh fabric is formed of a biologically compatible, flexible and strong implantable material.

The mesh fabric may employ a knit construction that provides relatively large openings or pores to ensure good visibility of the underlying anatomy without sacrificing mechanical properties of the mesh. The porous character of the fabric allows tissue infiltration to incorporate the prosthetic. The knitted fabric is sufficiently strong and structured to prevent or minimize potential pullout of anchoring fasteners, such as sutures, staples, tacks, and the like. The flexible repair fabric may promote an easy reduction in size for entry into the subject. In this manner, the flexible fabric may be collapsed into a slender configuration, such as a roll, which can be supported in, and advanced through, a narrow laparoscopic cannula for use in laparoscopic procedures.

The mesh fabric employs a relatively lighter weight, thinner, and/or more flexible fabric construction that may introduce less foreign body material into a patient as compared to other repair fabrics. The porous prosthetic repair fabric allows a prompt fibroblastic response through the interstices of the mesh, forming a secure fibrous/prosthetic layer. The fabric may promote a thinner and more compliant scar plate that may result in a relatively more comfortable soft tissue or muscle wall repair for a patient.

Figure 1:
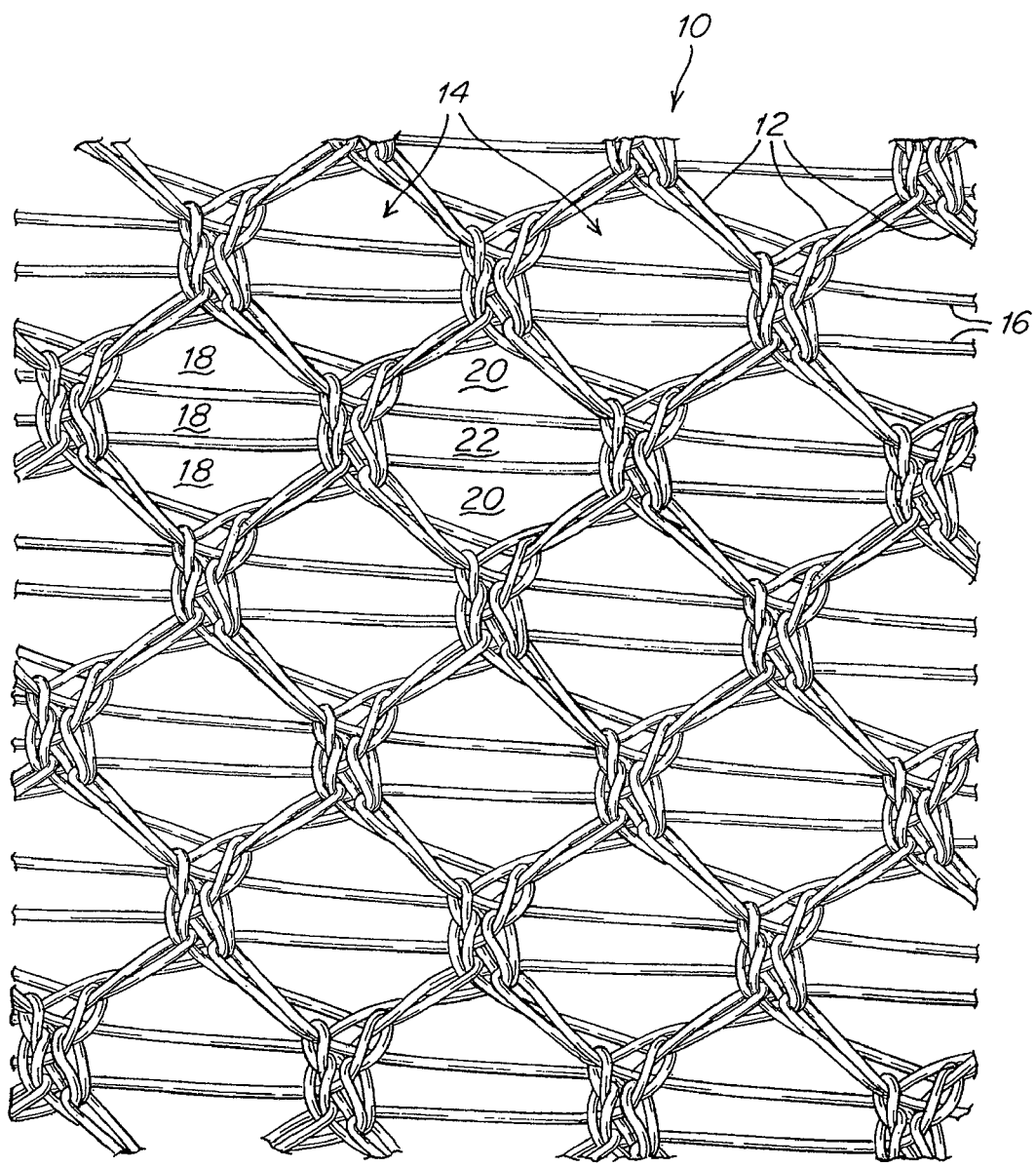
FIG. 1 is a magnified photomicrograph of a dual bar warp knit, mesh fabric according to an illustrative embodiment of the present invention.

In one illustrative embodiment shown in FIG. 1, the repair fabric comprises a knit mesh 10 including knitted strands of filaments 12 that define larger, primary pores 14 arranged in a uniform pattern. A pair of individual filaments 16 extend across the primary pores to define a plurality of smaller, secondary pores 18 therein.

In the illustrated embodiment, the primary pores 14 are bounded by knitted strands of filaments 12. However, it is to be appreciated that one of more boundaries of the primary pores 14 may be defined by individual filaments as would be apparent to one of skill in the art. As shown, the primary pores 14 may be generally diamond or square shaped, although aspects of the invention are not limited. In this regard, it is to be understood that other pore shapes are also contemplated, including, but not limited to, circular, non-circular, round, oval, hexagonal and the like, as would be apparent to one of skill in the art.

The prosthetic repair fabric may be constructed to increase flexibility and/or reduce the overall weight per unit area of the fabric. Such properties may facilitate an easier collapse of the repair fabric for introduction into a patient. These properties may also provide for easier manipulation of the repair fabric about the surgical site within the patient. In one illustrative embodiment, the primary pores 14 have an area of approximately 0.0089 to 0.0103 square inches. In this regard, less material may be used to produce a given area of mesh, which may result in a reduced weight mesh. Additionally, the generally greater spacing between the strands of filaments 12 that are associated with the larger primary pores 14 may also contribute to a more flexible mesh. It is to be appreciated, however, that the size of the primary pores may vary as would be apparent to one of skill in the art, as aspects of the invention are not limited in this respect.

For some applications, it may be desirable to provide secondary pores 18 within the primary pores 14. In one illustrative embodiment shown in FIG. 1, each primary pore 14 is subdivided into a plurality of secondary pores 18 by a pair of individual or single filaments 16. In the illustrative embodiment, the pair of filaments 16 divides the primary pore 14 into a pair of generally triangular secondary 20 pores and a generally rectangular secondary pore 22 that is positioned between the two generally triangular secondary pores 20. It is to be appreciated, however, that the shapes of secondary pores and/or numbers of secondary pores within each primary pore, if desired, may vary as would be apparent to one of skill in the art, as aspects of the invention are not limited in this respect.

In one illustrative embodiment as shown in FIG. 1, the pair of individual filaments 16 extend substantially parallel to one another across the primary pores 14. As illustrated, the pair of parallel filaments 16 may be generally in linear alignment with corresponding pairs of filaments in adjacent primary pores. However, it is to be understood that the individual filaments may be positioned and oriented in other suitable arrangements, as aspects of the present invention are not limited in this respect.

The prosthetic repair fabric may be constructed so as to be provisionally anchored to tissue or muscle using a wide variety of fasteners, such as sutures, staples, spiral tacks, Q-rings and the like. The individual filaments 16 that extend across the primary pores may provide additional features for engaging the fasteners used to anchor the fabric. It is to be appreciated that repair fabrics may be anchored to tissue and/or mesh with fasteners, such as spiral tacks and Q-ring constructs, that have relatively small features for engaging and holding the repair fabric in place. The smaller, secondary pores 18 associated with the individual filaments may provide for improved engagement with the fasteners in a manner that is sufficiently strong and structured to prevent or minimize pullout. In one illustrative embodiment, each secondary pore has an area of approximately 0.0022 to 0.0032 square inches. It is to be appreciated, however, that the size of the secondary pores may vary as would be apparent to one of skill in the art, as aspects of the invention are not limited in this respect.

In one illustrative embodiment, the knit mesh 10 may be produced in a lapping pattern by using two partially threaded guide bars to knit the pattern over three needles in a six course repeat. The fabric structure may be of an atlas type where each knitted end travels more than two needles, which may prevent unraveling of the mesh.

Figure 2A:
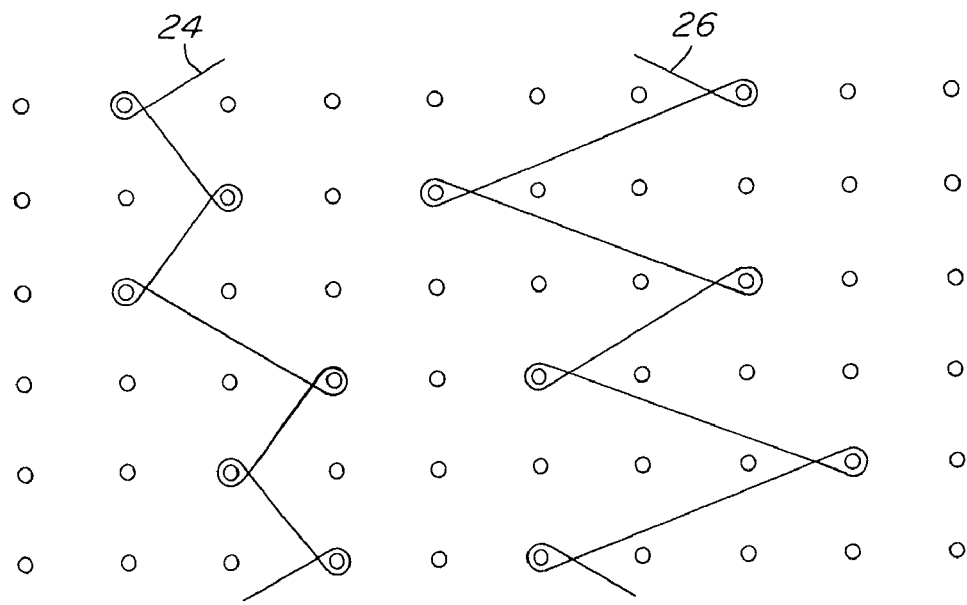
FIGS. 2A and 2B illustrate the chain lapping pattern for the mesh fabric of FIG. 1.
Figure 2B:
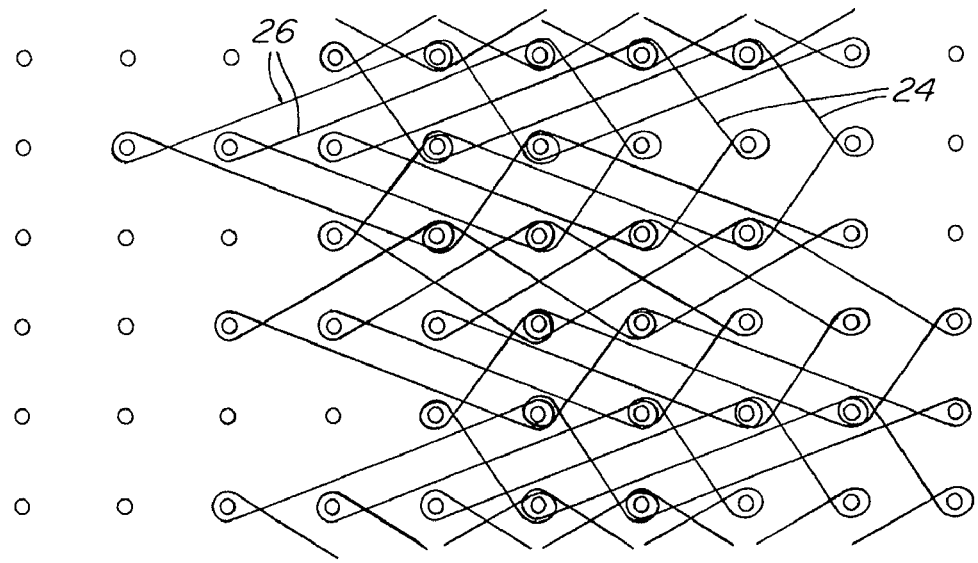

In one illustrative embodiment shown in FIGS. 2A and 2B, the repair fabric is a dual bar warp knit mesh structure produced using two guide bars moving according to a first bar pattern chain of 4/2 4/6 4/2 6/8 6/4 6/8 (identified as reference 24) and a second bar pattern chain of 6/8 2/0 6/8 4/2 8/10 4/2 (identified as reference 26). The mesh may be knitted on a single needle bar, 24 gauge Rachelle knitting machine. The mesh may be fabricated with approximately 34 to 36 courses per inch and approximately 12 to 17 wales per inch. It is to be appreciated, however, that the mesh fabric may be knitted using any suitable knit pattern as would be apparent to one of skill in the art, as aspects of the invention are not limited in this respect.

The knit mesh may be produced at various widths apparent to one of skill in the art, such as from 1 inch to 80 inches, depending on the intended application for which the repair fabric is being produced.

Following knitting, the fabric may be washed to remove foreign matter, such as residual processing lubricant. A cleaning agent, such as Triton X-100, may be used to aid in the removal of such foreign matter. Following washing, the mesh may be dried at a temperature lower than the heat set and melt temperatures of the material, as would be apparent to one of skill in the art.

Embodiments of the knit mesh may be heat set to impart a shape memory to the mesh and the prosthetic fabric formed of the mesh. In one illustrative embodiment, the fabric is heat set to have a generally planar shape memory. In this manner, after the fabric is collapsed and inserted into a patient, the fabric may revert back to the planar configuration for appropriate placement against tissue of the patient. It is to be appreciated that other embodiments of the fabric may be provided with a shape memory that corresponds to configurations different than planar, or to have no shape memory at all, as aspects of the invention are not limited in this regard.

If desired, the knit mesh may be heat set under tension, in a crochet hoop or tentering frame. The heat set may be applied while the mesh knit is being stretched in a particular direction to help set the mesh into a particular configuration. In one illustrative embodiment, the knit mesh is stretched in the cross machine knit direction and simultaneously allowed to partially relax or contract in the machine direction to a fixed point while heat is applied to set the mesh. It is to be understood, however, that other techniques apparent to one of skill in the art may be used to heat set the knit mesh, as aspects of the invention are not limited in this respect.

For some applications, it may be desirable to smooth the knitted mesh to reduce the texture or surface roughness of the mesh. In one illustrative embodiment, the knitted mesh is lightly pressed between a pair of plates which includes a heated plate that is pressed against the rough surface of the mesh to reduce high spots of the mesh and to heat set it to smooth its surface. It is to be appreciated, however, that the fabric may be smoothed using any suitable process apparent to one of skill in the art. For example, the fabric may be smoothed by passing the knitted mesh between a pair of heated rollers during the washing and drying process.

The filaments that are used to fabricate the repair fabric may contribute to the resulting mechanical properties of the fabric. In one illustrative embodiment, the repair fabric is knitted with filaments having a diameter of approximately 0.0045 to 0.0051 inches, and preferably a diameter of approximately 0.0048 inches. A filament of this diameter may contribute to an increased flexibility and reduced weight per unit area of the overall repair fabric. It is to be understood, however, that the fabric may be fabricated with filaments having any suitable diameter apparent to one of skill in the art that is suitable for a desired application, as aspects of the invention are not limited in this respect.

In one illustrative embodiment, the fabric has a thickness of approximately 0.017 to 0.022 inches, and preferably a thickness of approximately 0.017 to 0.019 inches. In one illustrative embodiment, the fabric has a weight per unit area of approximately 0.022 to 0.032 grams per square inch, and preferably a weight per unit area of approximately 0.027 to 0.030 grams per square inch. It is to be appreciated, however, that the fabric may be fabricated to have any thickness and/or weight per unit area apparent to one of skill in the art that is suitable for a desired application, as aspects of the invention are not limited in this respect.

In one illustrative embodiment, the filaments used to fabricate the mesh fabric comprise a polypropylene monofilament, which is inert in the presence of infection, is non-wettable and has a low foreign body reaction. In one illustrative embodiment, the monofilament is formed of Phillip's Polypropylene resin HGX—030 or Polypropylene resin HGX—030—01. In one embodiment, the monofilament has a denier of approximately 90 to 100. In one embodiment, the monofilament has a tenacity of approximately 6.0 to 8.5 grams/denier, and preferably a tenacity of approximately 7.25 grams/denier. It is to be appreciated, however, that filaments of different configurations, properties and/or materials may be employed to fabricate the fabric. For example, the filaments may comprise multifilaments or monofilaments having different mechanical characteristics as would be apparent to one of skill in the art, as aspects of the present invention are not limited in this respect.

EXAMPLES

The following examples are illustrative only and are not intended to limit the scope of the present invention.

Physical properties of a representative two bar warp knit mesh fabric produced from 0.0048 inch polypropylene monofilament according to the illustrative embodiment shown in FIGS. 1 and 2 (labeled Embodiment #1 in Table 1) were evaluated and compared to several known mesh fabrics. Physical and performance characteristics were tested including mesh thickness, pore size, mesh weight per unit area, suture pull out strength, burst strength, tear resistance, tensile (break) strength and elongation at break, and stiffness. Testing methodology and results appear below in Table 1, where mean results and ranges are reported from several test samples (ranges appear in parentheses).

Fabric samples were also tested and found to have a 5 mm spiral tack retention strength of approximately 2.4 to 6.2 lbs, and to have a mesh deflection of approximately 0.003 to 0.013 inches at a 5 lb load, approximately 0.032 to 0.042 inches at a 10 lb load, and approximately 0.114 to 0.140 inches at break.

Suture Pullout Strength: A sample of mesh measuring at least 0.5 inch×3 inches was prepared and clamped in the lower jaw of an MTS™ or equivalent tensile test machine. At least 1 inch of the mesh was exposed above the jaw. A spring steel wire with a diameter of approximately 0.019 inches was placed through the mesh to simulate a suture. The wire was placed 4±0.2 mm from the edge of the mesh. The wire suture was looped back and both ends were attached to the upper jaw of the tensile machine. The suture was then pulled at a rate of 5 inches per minute through the mesh starting with a minimum jaw separation of 1 inch. The peak force was recorded for ten samples tested in both the machine and cross directions of the mesh and the average force was calculated for each direction.

Pore Size: A sample of mesh was placed on an optical coordinate measurement device. The generally diamond or square shaped primary cell, which contains two generally triangular pores and a generally rectangular pore in the middle section, was measured dimensionally to the nearest 0.0001 inch. The area was calculated by taking 0.5 (L)×0.5 (W)×3.146. Ten randomly selected pores (not counting the pores formed by the loops or knots) were measured and a combined average was calculated.

Tensile (Break) Strength and Elongation at Break: A mesh sample measuring approximately 1 inch×6 inches was placed into the pneumatic jaws of an MTS™ tensile tester or equivalent device. The sample was oriented so that the knit direction being tested was parallel to the 6 inch length. The ends of the 6 inch sample were gripped in the lower and upper jaws of the tester. Starting with a minimum separation of 2 inches, the sample was pulled at a constant rate of 12 inches per minute until the sample broke. The peak load and elongation at break were recorded. Ten samples were tested in both the cross direction and the machine direction. The averages were then calculated for each direction.

Mesh Thickness: A sample of mesh measuring approximately 6 inches×6 inches was measured using a standard thickness snap gage with an approximate 0.38 inch diameter pressure foot that is lightly spring loaded. The thickness was measured by lowering the foot onto the mesh. Measurements were taken to the nearest 0.0001 inch at three locations across the mesh sheet and then averaged. Ten sheets of mesh were measured in total and a combined average was calculated.

Mesh Weight/Unit Area: Using a sample size of seven pieces of mesh that measured approximately 6 inches×6 inches (with a radiused corner), the total collective weight of the seven sheets was measured in grams to the nearest 0.0001 gram. The average weight was then calculated. The area was calculated by measuring the length and width dimensions taken to the nearest 0.001 inch, minus the area of the radiused corner. The average area was calculated for the seven pieces. The weight per unit area was calculated using the average weight and average unit area.

Burst Strength: This test method was derived from the ANSI/AAMI VP20-1994 Section 8.3.3.2 and ASTM Ball Burst method D3787-01. A mesh sample was placed on top of a circular O-ring measuring approximately 1 inch in diameter. The O-ring was seated in a grooved plate in a fixture with a hole in the middle of plate containing the O-ring. The fixture was attached to the lower jaw in an MTS™ or equivalent test machine. The plate with the mesh was raised and clamped against an upper plate in the fixture, compressing the mesh sample. The upper plate also contained a hole with the same diameter as the lower plate. The holes in the fixture plates are dimensioned to be just slightly larger than and to accept a rounded ball tipped rod that has a 0.38 inch diameter tip. The rod was connected to an upper jaw of the test machine that was moved down through the sample at a constant rate of 12 inches per minute. The peak load was recorded for each of ten samples. The average burst strength was then calculated based on the peak loads for the ten samples.

Tear Resistance: A mesh sample measuring approximately 2 inches×2 inches was prepared. A 1 inch slit was cut in one side (the direction to be tested) at the mid point to form two mesh sections. One section of mesh was clamped in the lower jaw of a pneumatic fixture and the other was clamped in the top jaw of the fixture. Starting with the jaws at a minimum spacing of 1 inch, the mesh was pulled at a rate of 12 inches per minute until the tear was completed. The peak force was recorded. Ten samples were tested in the cross, machine direction, and the diagonal direction. The averages were then calculated for each group direction.

Stiffness: The stiffness test was based on the stiffness of a fabric by a circular bend procedure (see ASTM Standard D4032-94). A mesh sample measuring approximately 4 inches×4 inches was prepared and tested. The mesh was placed on top of a plate with the rougher side of the mesh facing down. The plate included a 1.5 inch diameter through hole with a chamfered lead-in. The mesh was pushed or plunged down into this plate by a 1 inch diameter plunger. The plunger was set to travel at a constant rate of 12 inches per minute. The plunger traveled 1.5 inches below the mesh surface and the peak load was recorded. Ten samples were tested and the average was calculated for the entire group.

TABLE I

| | Embodiment #1 | BARD MESH | Ethicon PROLENE Soft Mesh | Ethicon MERSILENE Mesh |
|---|---|---|---|---|
| Suture Pullout (lbs) | | | | |
| Machine Direction | 8.2 (7.1-9.6) | 12.16 (9.14-14.29) | 5.4 (3.9-6.6) | 1.75 (1.33-2.33) |
| Cross Direction | 6.7 (4.8-8.0) | 7.97 (6.87-9.73) | 6.3 (5.2-8.0) | 2.17 (1.53-2.47) |
| Pore Size (inches$^2$) | | | | |
| Large Cell | 0.00975 (0.00891-0.01033) | n/a | 0.00941 (0.00803-0.0104) | n/a |
| Small Pore | 0.00246 (0.00220-0.00320) | 0.00085 (0.00062-0.00100) | 0.00386 (0.00357-0.00432) | 0.00123 (0.00104-0.00139) |
| Tensile (Break) Strength (lbs) | | | | |
| Machine Direction | 11.93 (10.07-15.20) | 21.7 (13.9-26.8) | 22.11 (18.01-26.8) | 22.7 (20.3-26) |
| Cross Direction | 43.84 (35.26-48.38) | 49.9 (42.7-58.0) | 21.97 (19.00-26.01) | 10.5 (8.9-12) |
| Elongation at Break (%) | | | | |
| Machine Direction | 61.8 (26.0-94.5) | 43 (30-50) | 69.25 (59-79.5) | 24 (22-26) |
| Cross Direction | 49 (40.5-54) | 30 (25-35) | 54.5 (49.5-63.5) | 25 (21-29) |
| Mesh Thickness (Inches) | | | | |
| | 0.0174 (0.0168-0.0172) | 0.0278 (.0273-0.0296) | 0.0168 (0.0163-0.0172) | 0.0203 (0.0200-0.0204) |
| Weight/Unit Area (gms/inches$^2$) | | | | |
| | 0.0282 (0.0274-0.0293) | 0.0680 (0.065-0.071) | 0.0287 (0.0273-0.0296) | 0.0274 (0.026-0.030) |
| Tear Resistance (lbs) | | | | |
| Machine Direction | 6.36 (5.35-6.96) | 10.31 (7.27-14.68) | 6.05 (4.70-7.15) | 1.53 (1.33-1.87) |
| Cross Direction | 5.46 (4.84-6.30) | 11.01 (9.41-13.68) | 5.72 (4.78-6.43) | 1.50 (1.33-1.74) |
| Diagonal Direction | 5.94 (5.18-6.82) | 10.83 (7.20-14.26) | 5.97 (5.27-6.65) | 1.44 (1.27-1.60) |
| Stiffness (lbsf) | | | | |
| | 0.311 (0.235-0.348) | 0.648 (0.499-0.922) | 0.225 (0.181-0.317) | 0.043 (0.027-0.063) |
| Ball Burst (3/8" ball, lbs) | | | | |
| | 29.17 (25.02-34.94) | 67.98 (63.64-74.21) | 31.01 (26.58-35.13) | 18.1 (16.0-19.4) |
| Mesh Construction | | | | |
| Courses (per inch) | 34.6 (34-36) | 54.5 | 45.6 (44-48) | 72 |
| Wales (per inch) | 14.1 (12-17) | 15.5 | 16.2 (16-18) | 47 |

It should be understood that the foregoing description of the invention is intended merely to be illustrative thereof and that other equivalents, embodiments and modifications of the invention are within the scope of the invention recited in the claims appended hereto.

What is claimed is:

1. An implantable prosthetic repair fabric, comprising: a biologically compatible, implantable dual bar warp knit mesh including a plurality of primary pores defined by knitted strands of filaments, each primary pore including a plurality of secondary pores that are defined by a pair of filaments extending across each primary pore, the knit mesh produced with closed loops according to a first bar pattern chain of 4/2 4/6 4/2 6/8 6/4 6/8 and a second bar pattern chain of 6/8 2/0 6/8 4/2 8/10 4/2.

2. The implantable prosthetic repair fabric according to claim 1, wherein the mesh is formed of knitted monofilaments.

3. The implantable prosthetic repair fabric according to claim 2, wherein the monofilaments include polypropylene monofilament.

4. The implantable prosthetic repair fabric according to claim 3, wherein the monofilament has a diameter of approximately 0.0045 to 0.0051 inches.

5. The implantable prosthetic repair fabric according to claim 3, wherein the monofilament has a diameter of approximately 0.0048 inches.

6. The implantable prosthetic repair fabric according to claim 3, wherein the monofilament has a denier of approximately 90 to 100.

7. The implantable prosthetic repair fabric according to claim 3, wherein the monofilament has a tenacity of approximately 6.00 to 8.50 grams per denier.

8. The implantable prosthetic repair fabric according to claim 3, wherein the monofilament has a tenacity of approximately 7.25 grams per denier.

9. The implantable prosthetic repair fabric according to claim 3, wherein the mesh has a knit construction that includes approximately 34 to 36 courses per inch and approximately 12 to 17 wales per inch.

10. The implantable prosthetic repair fabric according to claim 1, wherein the mesh has a weight per unit area of approximately 0.027 to 0.030 grams per square inch.

11. The implantable prosthetic repair fabric according to claim 1, wherein the mesh has a thickness of approximately 0.017 to 0.019 inches.

* * * * *